United States Patent

Leidreiter et al.

Patent Number: 5,750,097
Date of Patent: May 12, 1998

[54] USE OF DIACETYL TARTRATE ESTERS OF FATTY ACID GLYCERIDES AS HAIR CONDITIONER ADDITIVES

[75] Inventors: Holger Leidreiter; Felix Müller, both of Essen, Germany

[73] Assignee: Th. Goldschmidt AG, Essen, Germany

[21] Appl. No.: 399,796

[22] Filed: Mar. 7, 1995

[30] Foreign Application Priority Data

Mar. 15, 1994 [DE] Germany .................. 44 08 668.7

[51] Int. Cl.$^6$ ...................................... A61K 7/08
[52] U.S. Cl. .............. 424/70.1; 424/70.21; 424/70.22; 424/70.27; 424/70.31
[58] Field of Search ................. 424/70.1, 70.21, 424/70.22, 70.27, 70.31

[56] References Cited

U.S. PATENT DOCUMENTS 2,236,516  4/1941  Cahn et al. .................. 260/410

OTHER PUBLICATIONS

Emulgatoren als Zusatzstoffe für Lebensmittel by Von G. Schuster & W. Adams, Illertissen (pp. 265–272).

*Primary Examiner*—Jyothsan Venkat
*Attorney, Agent, or Firm*—Anderson, Kill & Olick, P.C.

[57] ABSTRACT

The invention relates to the method of preparing an agent for a hair care preparation based on diacetyl tartrate esters of fatty acid glycerides of the following general formula:

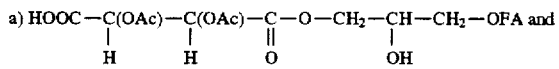

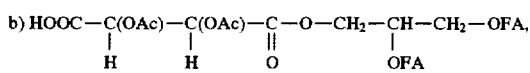

wherein
Ac is the acetyl group,
FA is the acyl group of a fatty acid or of a fatty acid mixture with 8 to 18 carbon atoms, and
a) and b) being present in a ratio by weight of 100:0 to 60:40.

2 Claims, No Drawings

USE OF DIACETYL TARTRATE ESTERS OF FATTY ACID GLYCERIDES AS HAIR CONDITIONER ADDITIVES

FIELD OF THE INVENTION

The invention relates to a method of preparing an agent for a hair care preparation based on diacetyl tartrate esters of fatty acid glycerides with improved conditioning properties as well as to the agent for the hair care preparation thus obtained.

BACKGROUND INFORMATION AND PRIOR ART

It is well known that modern hair treatments, such as permanent waving, bleaching, tinting, dyeing or shampooing can affect the natural nature of the hair, with the consequence that the hair is dry, brittle and difficult to handle. This can be caused, on the one hand, due to the degreasing of the hair and the scalp. On the other hand, hair dyes and alkaline media, such as permanent waving materials, can decisively change the structure of the hair. The surface becomes duller and the whole structure of cortex and cuticula is weakened so that the hair becomes brittle and withstands only slight tensile forces. Such damage to the hair is also caused by natural ageing, bleaching by light, frequent washing and mechanical wear.

Therefore, to reduce these effects, hair conditioners are added to cosmetic hair-treating agents, such as shampoos and rinses so as to improve the structure of the hair and, with that, improve the combability and the handle of the wet hair, as well as reduce knotting directly after use. Thus, the dry hair should have gloss, as well as good handling and combing properties. A further aim is to reduce electrostatic charging.

In the state of the art, numerous materials of different types are proposed as hair conditioners, namely acrylate, styrene, vinyl or silicone derivatives, products from natural materials such as plant extracts or derivatized products, and animal or vegetable fat products. However, it has proven to be difficult to attain at a high level, as far as possible, all the care effects mentioned.

OBJECT OF THE INVENTION

An object of the present invention is a method of preparing an agent for a hair care preparation with the widest possible spectrum of conditioning and care-taking properties of high quality. Another object of the invention is the agent for the hair care preparation thus obtained.

SUMMARY OF THE INVENTION

This objective is accomplished by using diacetyl tartrate esters of fatty acid glycerides of the general formula:

a) HOOC—C(OAc)—C(OAc)—C—O—CH$_2$—CH—CH$_2$—OFA and
       |        |        ||             |
       H      H      O            OH b) HOOC—C(OAc)—C(OAc)—C—O—CH$_2$—CH—CH$_2$—OFA,
       |        |        ||             |
       H      H      O            OFA wherein Ac is an acetyl group, FA is an acyl group of a fatty acid or of a fatty acid mixture with 8 to 18 carbon atoms, and a) and b) being present in a ratio by weight of 100:0 to 60:40, as an agent for a hair care preparation for the care of the hair.

For the preparation of the diacetyl tartrate esters, preferably monoglycerides and diglycerides of linear fatty acids with 8 to 18 carbon atoms are used, particularly the fatty acids and fatty acid mixtures with 16 to 18 carbon atoms obtained from natural fats, or optionally, from hydrogenated fatty acids and fatty acid mixtures with 16 to 18 carbon atoms. Examples are palmitic, stearic, oleic, linoleic and linolenic acids.

Isostearic acid, which can be produced industrially, can be used in the same way.

Preferably, the distilled fatty acid monoglycerides are used, since as the proportion of diglycerides increases, the correspondingly obtained diacetyl tartrate esters, with their higher hydrophobicity, can cause solubility problems during the production of the conditioning formulations.

All the optical isomers can be used in the same way as tartaric acid. Meaningfully, the naturally occurring 2R,3R-tartaric acid is preferred.

The ester, which is to be used pursuant to the invention, is synthesized as described, for example in the DE-C-20 21 565 or in the *ZFL Zeitschrift fuer Lebensmittel-Technologie und Verfahrenstechnik*, volume 31, number 6, 1980. Due to the method of synthesis and the use of industrial products, it is possible that by-products, such as diacetyl tartrate mono-glycerides or monodiacetyl tartrate monoacetate monoglycerides, are contained in the desired product.

For example, diacetyl tartrate esters on the basis of glycerin stearate (diacetyl tartrate ester A) or on the basis of glycerin laurate (diacetyl tartrate ester B) can be synthesized. To make them easier to handle, these products can also be used in dilute or compounded form. For this purpose, all conventional additives in cosmetics come into consideration. Solvents, such as alcohols, glycols, oils, or also water, can be used.

The diacetyl tartrate esters can be present in dissolved or dispersed forms in these compounds. In the latter case, one or more dispersants is necessary as an additive for the production and stabilization of the dispersion. In particular, the combination with other conditioners, such as organic polymers and/or silicone derivatives is advantageous, since it is known from experience that such combinations can act synergistically.

The diacetyl tartrate esters, which are to be used pursuant to the invention, can be used in various forms. As care additive in a hair rinse, they can be combined without any problems with surface-active substances in the form of an aqueous preparation.

In this connection, quaternary ammonium salts are particularly suitable.

One such formulation for the after-treatment of washed hair can have the following composition:

EXAMPLE A (Hair Rinse for Slightly Overtaxed, Normal Hair)

| (hair rinse for slightly overtaxed, normal hair) | |
|---|---|
| Cetyl alcohol/stearyl alcohol with 25 moles of ethylene oxide | 1.5% |
| Glycerin monostearate/distearate | 1.5% |
| Cetyl alcohol | 2.0% |
| Diacetyl tartrate B | 1.0% |
| Polyether-modified polydimethylsiloxane | 0.4% |
| Glycerin | 2.0% |
| Citric acid | 0.2% |

EXAMPLE B (Hair Remedy for Dry, Fine Hair)

| (hair remedy for dry, fine hair) | |
|---|---|
| Cetyl alcohol/stearyl alcohol with 25 moles of ethylene oxide | 1.5% |
| Glycerin monostearate/distearate | 1.5% |
| Cetyl alcohol | 2.0% |
| Alkyl-modified polydimethylsiloxane | 0.4% |
| Diacetyl tartrate B | 1.0% |
| Polyether-modified polydimethylsiloxane | 0.4% |
| Polydimethylsiloxane, modified with quaternary ammonium groups | 2.0% |
| Glycerin | 2.0% |
| Citric acid | 0.2% |
| Water plus dyes and preservatives. | 88.0% |

(hair rinse for slightly overtaxed, normal hair)

| Water plus dyes and preservatives; | 91.4% |
|---|---| or

Usually, various additives, such as oils, fatty acids and their esters, nonionic or amphoteric surface-active substances, disinfectants, perfumes, dyes and carrier materials, etc., are added to such preparations.

In the same way, the diacetyl tartrate esters, which are to be used pursuant to the invention, can be added to shampoo formulations based on conventional surface-active agents.

Such formulations, as a rule, are based on

- at least one detergent surfactant (at least one or two anionic, an amphoteric or zwitterionic surfactant, as well as nonionic surfactants),
- low molecular weight or polymeric surfactant additives for adjusting the rheological behavior,
- additives that provide a lustrous or opaque appearance,
- cationic, anionic and/or nonionic conditioners,
- auxiliaries, such as dyes, preservatives, acids, bases and complexing agents, and
- water.

The diacetyl tartrate esters of fatty acid glycerides are used in amounts of 0.1 to 10% by weight.

EXAMPLE C (Conditioning Shampoo for Normal Hair)

| (conditioning shampoo for normal hair) | |
|---|---|
| Diacetyl tartrate ester A | 2.0% |
| Glycerin monococoate with 7 moles of ethylene oxide | 3.0% |
| Sodium lauryl ether sulfate, 2.5 moles of ethylene oxide, 28%* | 40.0% |
| Water | 43.2% |
| Coconut oil fatty acid amidopropyl-betaine, 38% | 10.0% |
| Glycerin cocoate, oleate with 18 moles of ethylene oxide | 1.3% |
| Sodium chloride plus dyes and preservatives; | 0.5% |

EXAMPLE D (Conditioning Shampoo for Dry Hair)

| (conditioning shampoo for dry hair) | |
|---|---|
| Diacetyl tartrate ester B | 1.1% |
| Cationic guar (galactomannan) | 0.3% |
| Glycerin laurate with 30 moles of ethylene oxide | 3.0% |
| Sodium lauryl ether sulfate, 2.5 moles ethylene oxide, 28%* | 20.0% |
| Alkyl polyglucoside with $C_{12}$ to $C_{18}$ alkyl groups** | 12.0% |
| Water | 49.2% |
| Polydimethylsiloxane, modified with quaternary ammonium groups | 0.5% |
| Coconut fatty acid amidopropylbetaine, 38% | 9.0% |
| Flowable lustrous dispersion based on ethylene glycol distearate | 3.0% |
| Glycerin cocoate/oleate with 18 moles of ethylene oxide | 0.9% |
| Sodium chloride plus dyes and preservatives; | 1.0% |

*Commercially obtainable, for example, under the name of Texapon N25 (Henkel, Duesseldorf)
**Commercially obtainable, for example, under the name of Plantaren 1200 (Henkel, Duesseldorf)

EXAMPLE E (Conditioning Shampoo for Sensitive Scalp)

| (conditioning shampoo for sensitive scalp) | |
|---|---|
| Diacetyl tartrate ester A | 1.0% |
| Glycerin monococoate with 7 moles of ethylene oxide | 1.0% |
| Glycerin laurate with 30 moles of ethylene oxide | 3.0% |
| Polyether-modified polydimethylsiloxane | 0.5% |
| Nonionic polymeric thickener based on polyacrylate copolymers | 1.5% |
| Lauryl ether sulfosuccinate, 40%*** | 10.0% |
| Sodium lauryl ether sulfate, 2.5 moles ethylene oxide, 28%* | 12.0% |
| Water | 51.0% |
| Coconut fatty acid amidopropylbetaine, 38% plus dyes and preservatives. | 20.0% |

*** Commercially obtainable, for example, under the name of Elfanol 616 (Akzo, Dueren)

The diacetyl tartrate ester A dissolves in surfactant formulations to form a clear solution and therefore does not affect the foam height. The diacetyl tartrate ester B, when dissolved in surfactant formulations, usually does not form a clear solution and causes a slight thickening of the foam; however, it has more effective care and conditioning properties than does the diacetyl tartrate A.

The diacetyl tartrate esters, which are to be used pursuant to the invention, are distinguished by a series of excellent conditioning properties.

For example, the hair, treated therewith, has good combability as well as good handle properties in the wet state. Moreover, the tendency to knot is slight. Good combability and handle properties are also achieved with dry hair.

After it has been dried, the hair achieves a gloss effect and electrostatic charging is reduced.

The inventive use of diacetyl tartrate esters in hair care preparations such as is equally suitable for all types of hair. The advantage of the inventive use of diacetyl esters becomes particularly clear when the hair is evaluated in the condition after drying. Particularly preferred is the use with dry (in the sense of not being very oily) or fine hair, since the missing natural sebum of the scalp and the deficient strength of the hair can be compensated for in an outstanding manner here. However, a negative over-oiling effect is not observed with normal or oily hair. This may be attributed to the fact that diacetyl tartrate ester is less substantive with respect to oily hair and more substantive with respect to the surface proteins of oil-free hairs.

It must be emphasized that, pursuant to the invention, conditioner additives are prepared which cover the whole spectrum of care properties. For example, the combability of the hair after drying is improved; however, the hairdressing properties and the handling are not affected negatively. This is not always the case with conditioners of the state of the art, since these, when they improve the combability, increase the sliding ability and with that, decrease the stability of a hairstyle and have a negative effect on the handling of the hair.

The above-described properties were found in comparison experiments with conditioning shampoos and strains of Indo-European hair.

| Example | F | G | H | I |
|---|---|---|---|---|
| Diacetyl tartrate ester B | 2.0% | — | — | — |
| Quaternized cellulose | — | 2.0% | — | — |
| Cationic guar (galactomannan) | — | — | 2.0% | — |
| Polydimethylsiloxane, modified with quaternary Ammonium groups | — | — | — | 2.0% |
| Glycerin monococoate with 7 moles of ethylene oxide | 3.0% | 3.0% | 3.0% | 3.0% |
| Sodium lauryl ether sulfate, 2.5 moles ethylene oxide, 28% | 40.0% | 40.0% | 40.0% | 40.0% |
| Water | 43.2% | 43.2% | 43.2% | 43.2% |
| Coconut fatty acid amidopropylbetaine, 38% | 10.0% | 10.0% | 10.0% | 10.0% |
| Cocoate/oleate esters of glycerin with 18 moles of ethylene oxide | 1.3% | 1.3% | 1.3% | 1.3% |
| Sodium chloride | 0.5% | 0.5% | 0.5% | 0.5% |

Grades of 0 to 4 were given in the comparison tests, 0 being the lowest grade (deficient) and 4 the highest (very good).

In a comparison of the four shampoos F, G, H and I, the following grades were the averages from 10 test subjects.

| Example | F | G | H | I |
|---|---|---|---|---|
| In wet hair: | | | | |
| Knotting | 2.2 | 1.5 | 1.2 | 2.6 |
| Combability | 2.2 | 1.6 | 1.2 | 2.4 |
| Handle | 2.2 | 1.9 | 1.2 | 2.2 |
| In dried hair: | | | | |
| Combability | 2.2 | 1.5 | 1.2 | 2.6 |
| Handle | 2.2 | 1.6 | 1.2 | 2.4 |
| Gloss | 2.2 | 2.0 | 2.0 | 1.8 |

In this comparison, a slightly better grade was achieved only for the evaluation of the wet hair which had been treated with the cationic silicone derivative. In all other comparisons, better results were achieved with the inventive use of diacetyl tartrate esters.

As already stated, a combination of one or several conditioning agents with the diacetyl tartrate esters can be used to achieve a conditioning effect, which is improved further and expanded in its spectrum.

Because of the already known use of diacetyl tartrate esters of fatty acid monoglycerides as baking aids (DE-C-20 21 565), the physiological compatibility of the hair conditioning agents, obtained pursuant to the invention, is easily achieved.

We claim:

1. A hair care composition containing 0.1 to 10% by weight of a conditioning agent comprising:

a) 60 to 100% by weight of

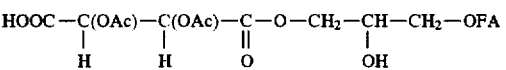

and b) 40 to 0% by weight of

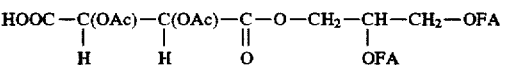

wherein

Ac is an acetyl group, and

FA is an acyl group of a fatty acid or of a fatty acid mixture with 8 to 18 carbon atoms c) detergent surfactant selected from the group consisting of anionic, amphoteric, zwitterionic, and nonionic surfactant and d) water.

2. A method of preparing an agent for a hair care preparation based on diacetyl tartrate esters of fatty acid glycerides, comprising the steps of mixing 60 to 100% by weight of a) 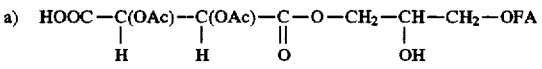

40 to 0% by weight of b) 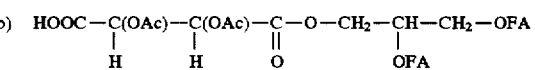

wherein

Ac is an acetyl group, and

FA is an acyl group of a fatty acid or of a fatty acid mixture with 8 to 18 carbon atoms c) detergent surfactant selected from the group consisting of anionic, amphoteric, zwitterionic, and nonionic surfactant and d) water.

* * * * *